(12) United States Patent
Servidio

(10) Patent No.: US 9,861,372 B2
(45) Date of Patent: Jan. 9, 2018

(54) PROSTHETIC IMPLANT AND ASSOCIATED INSTRUMENTS

(75) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 422 days.

(21) Appl. No.: 13/117,397

(22) Filed: May 27, 2011

(65) Prior Publication Data

US 2012/0303122 A1 Nov. 29, 2012

(51) Int. Cl.
- *A61F 2/08* (2006.01)
- *A61F 2/38* (2006.01)
- *A61B 17/15* (2006.01)
- *A61B 17/14* (2006.01)

(52) U.S. Cl.
CPC .......... *A61B 17/157* (2013.01); *A61B 17/142* (2016.11); *A61F 2/389* (2013.01)

(58) Field of Classification Search
CPC .......... A61F 2/389; A61F 2/38; A61F 2/3859; A61F 2/30; A61F 2/36; A61F 2/28; A61F 2002/3863; A61F 2002/4205
USPC ............................................. 623/20.14–20.36
See application file for complete search history.

(56) References Cited

U.S. PATENT DOCUMENTS

| | | | |
|---|---|---|---|
| 3,837,009 A * | 9/1974 | Walker | A61F 2/385 623/20.26 |
| RE29,757 E | 9/1978 | Helfet | |
| 4,224,696 A | 9/1980 | Murray et al. | |
| 4,728,332 A | 3/1988 | Albrektsson | |
| 4,808,185 A * | 2/1989 | Penenberg | A61B 17/1624 623/20.29 |
| 4,919,671 A | 4/1990 | Karpf | |
| 5,071,438 A * | 12/1991 | Jones et al. | 623/20.29 |
| 5,176,710 A * | 1/1993 | Hahn et al. | 623/20.32 |
| 6,428,577 B1 * | 8/2002 | Evans et al. | 623/20.29 |
| 6,641,614 B1 | 11/2003 | Wagner et al. | |
| 6,866,684 B2 | 3/2005 | Fell et al. | |
| 7,160,330 B2 | 1/2007 | Axelson, Jr. et al. | |
| 7,462,199 B2 | 12/2008 | Justin et al. | |
| 7,524,334 B2 | 4/2009 | Haidukewych | |
| 7,998,205 B2 * | 8/2011 | Hagen | A61F 2/38 623/14.12 |
| 2002/0022890 A1 | 2/2002 | Jacobsson et al. | |
| 2003/0100953 A1 | 5/2003 | Rosa et al. | |
| 2004/0006393 A1 | 1/2004 | Burkinshaw | |
| 2004/0107000 A1 | 6/2004 | Felt et al. | |
| 2004/0148030 A1 | 7/2004 | Ek | |
| 2004/0204766 A1 | 10/2004 | Siebel | |
| 2005/0027365 A1 | 2/2005 | Burstein et al. | |
| 2005/0125068 A1 * | 6/2005 | Hozack | A61F 2/389 623/20.32 |

(Continued)

*Primary Examiner* — Ann Schillinger
(74) *Attorney, Agent, or Firm* — Lerner, David, Littenberg, Krumholz & Mentilik, LLP

(57) ABSTRACT

A prosthetic implant comprises an articular surface and a bone contacting surface. The articular surface has a first concavity extending along a first curved axis and the bone contacting surface has a convexity extending along a second curved axis. Geometric relationships between the concavity of the articular surface and convexity of the bone contacting surface are described. A resulting feature of this implant is a bone contacting surface including both planar and non-planar geometries. Instrumentation and a method for the preparation of the non-planar bone surface are also described.

10 Claims, 13 Drawing Sheets

(56) References Cited

U.S. PATENT DOCUMENTS

| | | |
|---|---|---|
| 2006/0111726 A1 | 5/2006 | Felt et al. |
| 2008/0086210 A1 | 4/2008 | Fox |
| 2008/0183291 A1 | 7/2008 | Scheller et al. |
| 2008/0195216 A1 | 8/2008 | Philipp |
| 2008/0243263 A1 | 10/2008 | Lee et al. |
| 2009/0125108 A1 | 5/2009 | Linares |
| 2010/0305711 A1* | 12/2010 | McKinnon et al. ....... 623/20.32 |

* cited by examiner

PROSTHETIC IMPLANT AND ASSOCIATED INSTRUMENTS

BACKGROUND OF THE INVENTION

The present invention relates to implants and associated bone preparation instrumentation for use in joint replacement surgery. Knee arthroplasty is a known type of orthopaedic procedure typically aimed at correcting a patient condition through the implantation of a unicompartmental, bi-compartmental or tri-compartmental implant. In standard tri-compartmental or total knee arthroplasty, orthopedic implants replace areas of resected cartilage and bone on the distal femoral and proximal tibial bone. Typically, such an orthopaedic implant system may include a femoral component, a tibial component and a tibial insert that is assembled to the tibial component. Current tibial insert designs feature contoured articular surfaces designed to articulate with the femoral component. The respective geometries of the articular surface and femoral component are designed to result in a patient having a more "normal feeling" knee replacement. An example of such an insert design is described in U.S. Pat. No. 7,160,330, titled "Emulating Natural Kinematics in a Knee Prosthesis," which is hereby incorporated by reference herein. The evolution of these current designs focus on load transfer and kinematics between the femoral component and tibial insert. However, the bone contacting surface of the tibial baseplate has not been modified relative to the insert geometries. Therefore, while load transfer characteristics and function may be improved between the femoral implant and insert, the subsequent load transfer between baseplate and patient bone remains as a cooperation of simple planar contacting surfaces.

Loosening of a tibial baseplate is a well documented failure mode in orthopaedic registries for knee arthroplasty. The cause of baseplate loosening is multifactorial, but may in part be attributed to the various loads transferred to the tibial baseplate and bone contacting surface. Limitations in bone preparation instrumentation have kept the tibial baseplate bone contacting surface relatively planar, and any inaccuracies in bone preparation may lead to rocking, and eventually loosening of a tibial baseplate once implanted. As such, accuracy of preparation is a concern for both cemented and cementless implant designs, with cemented designs potentially being slightly more forgiving given the degree of correction of inaccurate bone cuts such cemented designs may provide.

Thus, there exists a need for a tibial baseplate with an increased resistance to tibial bone interface loading, as well as instrumentation for facilitating implantation of same.

SUMMARY OF THE INVENTION

One aspect of the invention is an implant comprising an articular surface that has a first apex. The implant further has a bone interface surface disposed opposite the articular surface. The bone interface surface has a convexity, a first curve and a second apex. Here, the first and second apexes define an axis, where the first curve bends about the axis and the convexity extends along the first curve.

Alternate embodiments of the implant may include one or any combination of the following elements. The articular surface has a concavity and a second curve, where the second curve bends away from the axis and the concavity extends along the second curve. The first and second curves are tangent to a sagittally oriented plane that extends through the articular and bone interface surfaces. The first and second curves are tangent to a sagittally oriented plane that extends through the articular and bone interface surfaces.

In yet alternate embodiments of the invention, any one or combination of the following elements may be further included to the implant. The first curve has a first center of curvature located within a first coronally oriented plane, the second curve has a second center of curvature located within a second coronally oriented plane, the first and second coronally oriented planes are essentially aligned. The first curve has a first curve has a first center of curvature located within a first coronally oriented plane, the second curve has a second center of curvature located within a second coronally oriented plane, the first and second coronally oriented planes are offset. The implant is designed to replace a portion of the proximal tibia. The articular surface and the bone interface surface are separate implants which are connected to form a single implant assembly.

Another aspect of the invention is an implant comprising an articular surface has a concavity, a first curve and a first apex. Further, it has a bone interface surface disposed opposite the articular surface, where the bone interface surface has a convexity, a second curve and a second apex. Here, the first and second apexes define an axis, the first curve bends away from the axis, the second curve bends about the axis, the concavity extends along the first curve and the convexity extends along the second curve.

Alternate embodiments of this aspect of the implant may include one or any combination of the following elements. The first and second curves are tangent to a sagittally oriented plane that extends through the articular and bone interface surfaces. The first curve has a first center of curvature located within a first coronally oriented plane; the second curve has a second center of curvature located within a second coronally oriented plane; and the first and second coronally oriented planes are essentially aligned. The first curve has a first curve has a first center of curvature located within a first coronally oriented plane; the second curve has a second center of curvature located within a second coronally oriented plane; and the first and second coronally oriented planes are offset. The implant is designed to replace a portion of the proximal tibia.

The articular surface and the bone interface surface are separate implants which are connected to form a single implant assembly.

Yet another aspect of the invention is a method of cutting a bone comprising fixing a first cutting guide with respect to the end of a long bone; making a planar resection of the bone with a first sawblade while referencing the first cutting guide; removing the first cutting guide from the end region of the bone; fixing a second cutting guide to the bone, the second cutting guide having a curved channel; removably attaching a third cutting guide to a second sawblade, the third cutting guide having a curved protrusion; making a non-planar resection by oscillating the second sawblade while movably engaging the protrusion of the third cutting guide with the curved channel of the second cutting guide; removing the protrusion of the third cutting guide from the channel of the second cutting guide; removing the second cutting guide from the bone; and implanting an implant directly onto the prepared bone.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
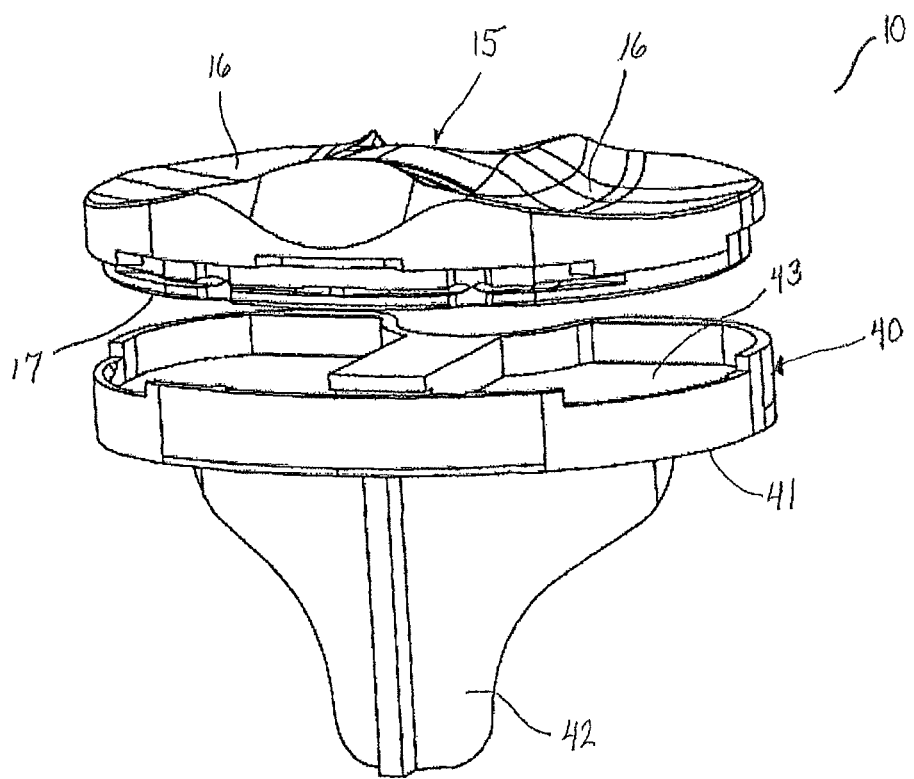
FIG. 1 is an exploded perspective view of a prior art modular tibial implant comprised of a tibial baseplate and tibial insert.

Referring to FIG. 1, there is shown a known tibial implant assembly 10 comprising an insert 15 and baseplate 40. This embodiment of a tibial implant assembly is designed for primary total knee arthroplasty. In this embodiment, baseplate has a proximal surface 43, a substantially planar bone contacting surface 41 and a keel 42 extending distally from bone contacting surface 41. Insert 15 has a proximal articular surface 16 and a distal surface 17. Distal surface 17 is essentially flat and is designed to mate with baseplate proximal surface 43, when assembled. It is understood that once implanted, the condyles of a femoral knee implant (not shown) would articulate with insert articular surface 16.

Figure 2:
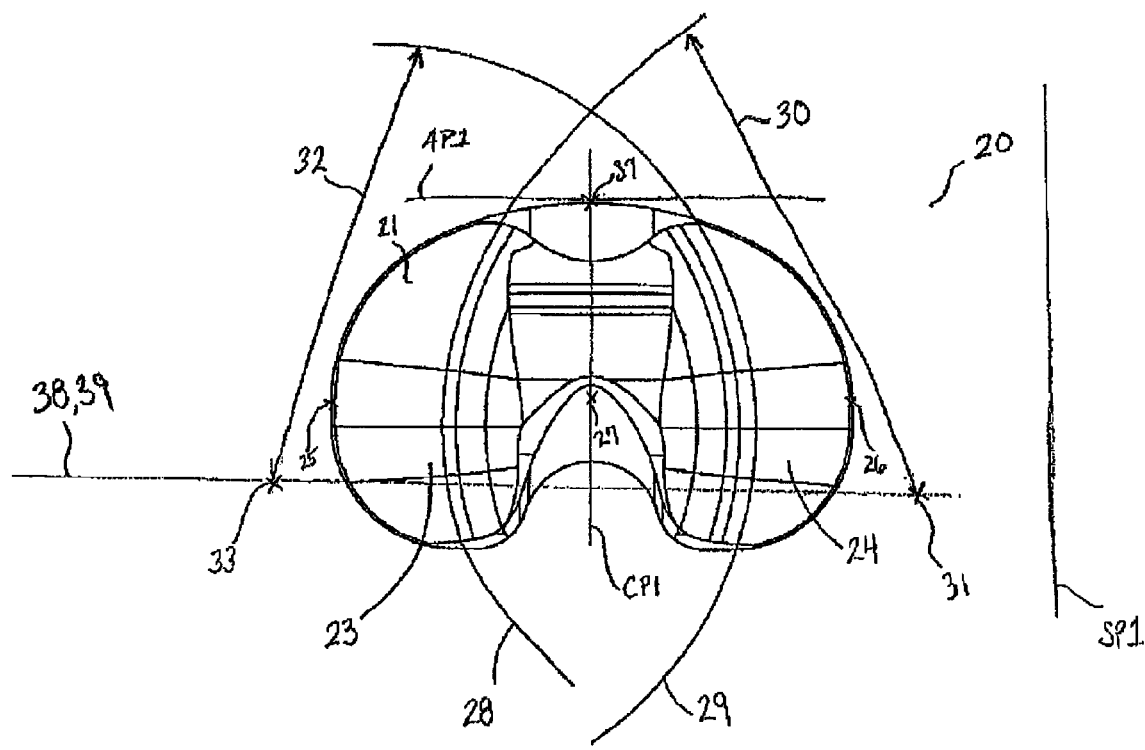
FIG. 2 is a top view of a tibial insert in accordance with one embodiment of the present invention
Figure 3:
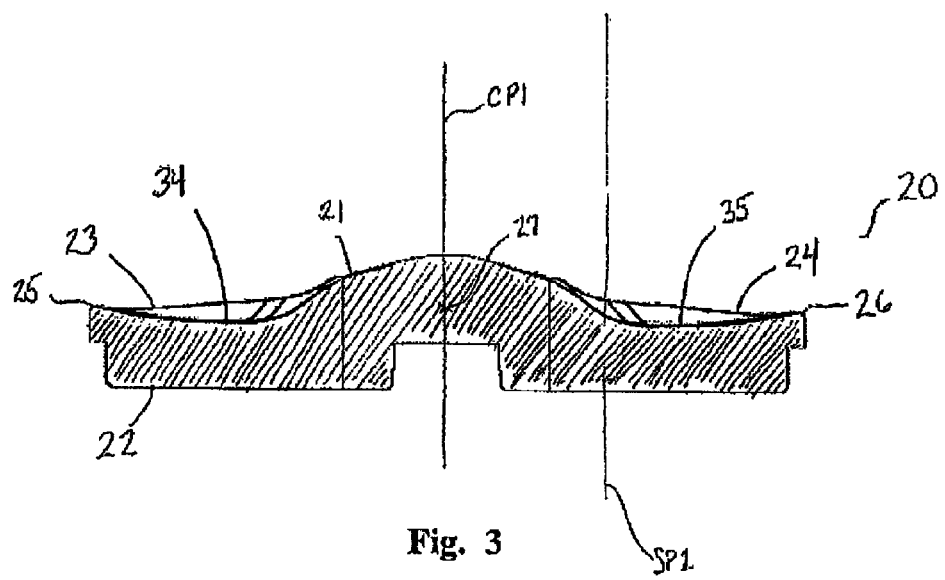
FIG. 3 is a cross-sectional front view of the tibial insert shown in FIG. 2.

A tibial insert 20 is shown in FIGS. 2 and 3, in particular, a top view of insert 20 is shown in FIG. 2 and a cross-sectional front view of insert 20 is shown in FIG. 3. Insert 20 has a proximal articular surface 21 and a distal surface 22. Proximal articular surface 21 has a medial region 23 designed to articulate with the medial condyle of a femoral implant and a lateral region 24 designed to articulate with the lateral condyle of a femoral implant. Medial region 23 includes a medial concavity 34 that extends along a medial curve 28 having a medial radius 30 and respective medial center of curvature 31. Similarly, lateral region 24 includes a lateral concavity 35 that extends along a lateral curve 29 having a lateral radius 32 and a respective lateral center of curvature 33.

Insert 20 further comprises an anterior apex 37, a medial apex 25, a lateral apex 26 and a center reference point 27. Anterior apex 37 is defined as the anterior most point of insert 20, while medial apex 25 is defined as the medial most point of insert 20 and lateral apex 26 is defined as the lateral most point of insert 20. Point 27 is centrally located on a theoretical axis extending between apexes 25 and 26. As shown, medial curve 28 bends away from medial apex 25 and lateral curve 29 bends away from lateral apex 26. In other words, both medial curve 28 and lateral curve 29 bend about center reference point 27. Still further, medial center of curvature 31 and lateral center of curvature 33 are located on opposing sides of a center plane CP1. Center plane CP1 is defined by a plane including center reference point 27, anterior apex 37, and being substantially perpendicular to distal surface 22.

Insert 20 further includes a medial plane 38, which is a plane including the medial center of curvature 31 and being substantially perpendicular to both center plane CP1 and distal surface 22. A lateral plane 39 is a plane including the lateral center of curvature 33 and being substantially perpendicular to both center plane CP1 and distal surface 22. In a preferred embodiment, medial plane 38 and lateral plane 39 are essentially aligned and thus are represented as a single plane in FIG. 2. In the embodiment shown, convexities 34 and 35 and curves 28 and 29 are respectively equivalent. Further, the medial center of curvature 31 and lateral center of curvature 33 are essentially aligned as described above. In other embodiments, such configurations may be varied, and thusly, planes 38 and 39 would not necessarily be aligned.

Figure 4:
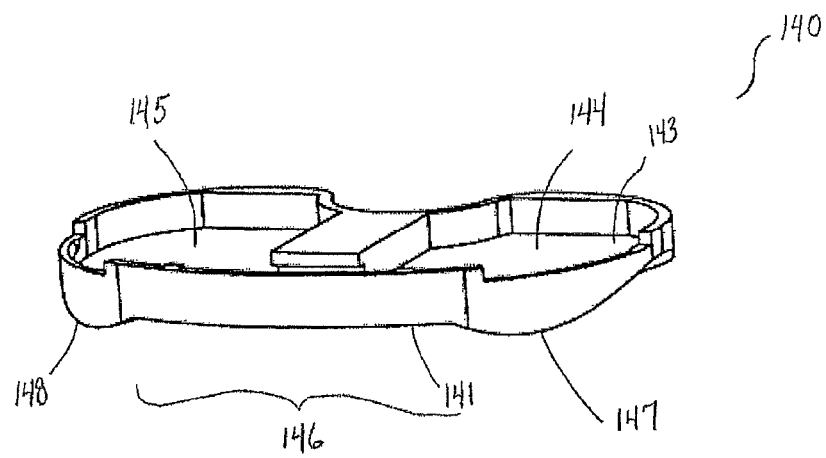
FIG. 4 is a perspective view of a tibial baseplate in accordance with one embodiment of the present invention.
Figure 5:
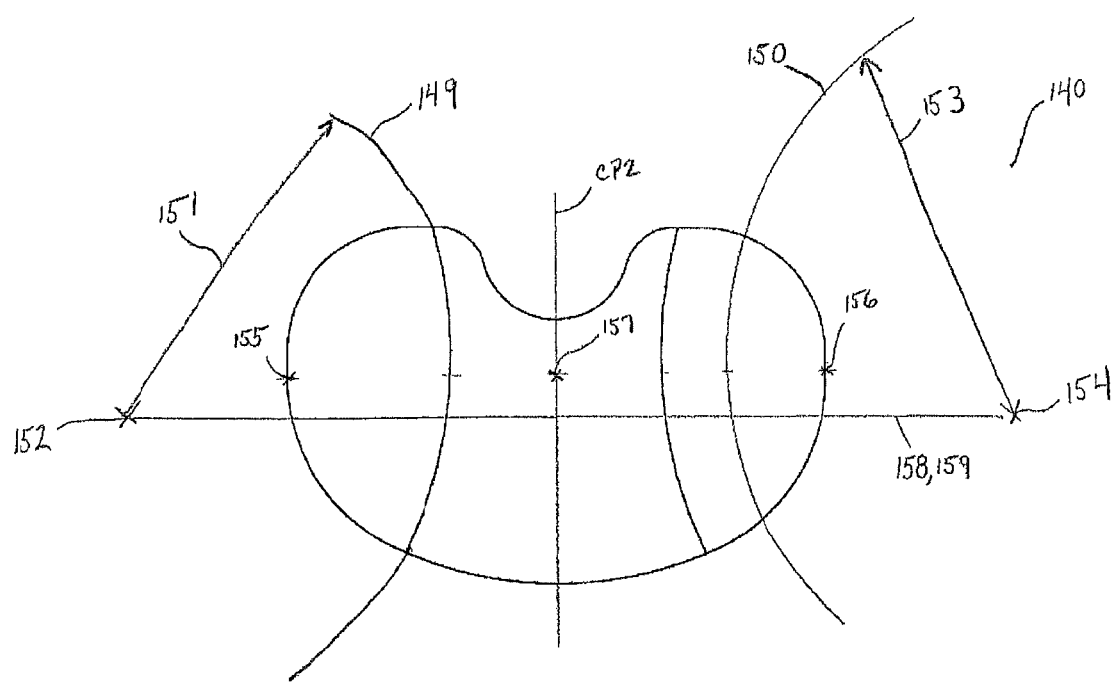
FIG. 5 is a bottom view of the tibial baseplate shown in FIG. 4.
Figure 6:
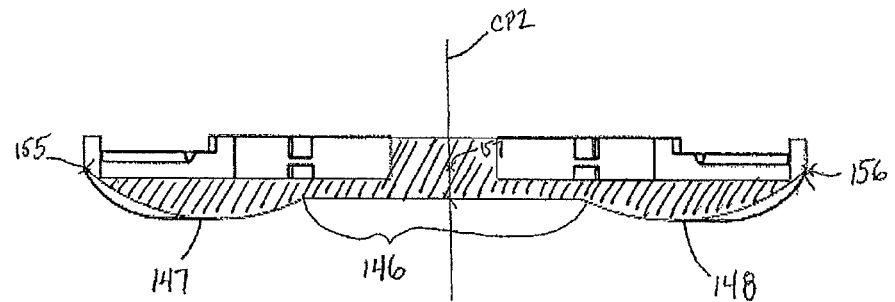
FIG. 6 is a cross-sectional front view of the tibial baseplate shown in FIG. 4.

FIGS. 4-6 illustrate a tibial baseplate 140 in accordance with one embodiment of the invention. Referring to FIG. 4, baseplate 140 includes a bone contacting surface 141 and a substantially flat proximal surface 143 having a medial aspect 144 and a lateral aspect 145. Proximal surface 143 is designed to mate with distal surface 22 of insert 20 when assembled. Bone contacting surface 141 is comprised of a substantially planar region 146, a medial convexity 147 and a lateral convexity 148. Medial and lateral convexities 147 and 148 are shown as essentially equivalent. In other embodiments, such convexities may be different, for instance, it is contemplated that medial convexity 147 may extend further distally than lateral convexity 148.

As shown in bottom view of baseplate 140 depicted in FIG. 5, medial convexity 147 extends about a medial curve 149 and lateral convexity 148 extends about a lateral curve 150. Medial curve 149 has a medial radius 151 and respective medial center of curvature 152. Similarly, lateral curve 150 has a lateral radius 153 and respective lateral center of curvature 154. Additionally, a center reference point 157 is centrally located on a theoretical axis extending between apexes 155 and 156, with the medial curve 149 and lateral curve 150 bending away from the center reference point 157. As in the above-discussed insert, apexes 155 and 156 represent the medial-most and lateral-most points, respectively.

In a preferred embodiment, medial radius 151 and lateral radius 153 are essentially equivalent. In alternate embodiments, radii 151 and 153 may be different. For example, medial radius 151 may be larger than lateral radius 153. Further, if both medial curve 149 and lateral curve 150 define respective planes, the planes may overlap, be essentially parallel, or have an alternate angular relationship.

Further in FIG. 5, there is shown a center plane CP2 which includes center reference point 157 and is substantially perpendicular to a plane extending through proximal surface 143. A medial plane 158 passing through medial center 152 and a lateral plane 159 passing through lateral center 154 are shown, each being substantially perpendicular to both center plane CP2 and proximal surface 143. In a preferred embodiment, medial plane 158 and lateral plane 159 are essentially aligned and thus are represented as a single line in FIG. 5. However, as in the above-discussed insert, these planes may vary. For instance, in one alternate embodiment, medial plane 158 may be substantially parallel to, but offset anteriorly from lateral plane 159. In another alternate embodiment, the lateral plane 159 may be substantially parallel to, but offset anteriorly from medial plane 158.

Figure 7:
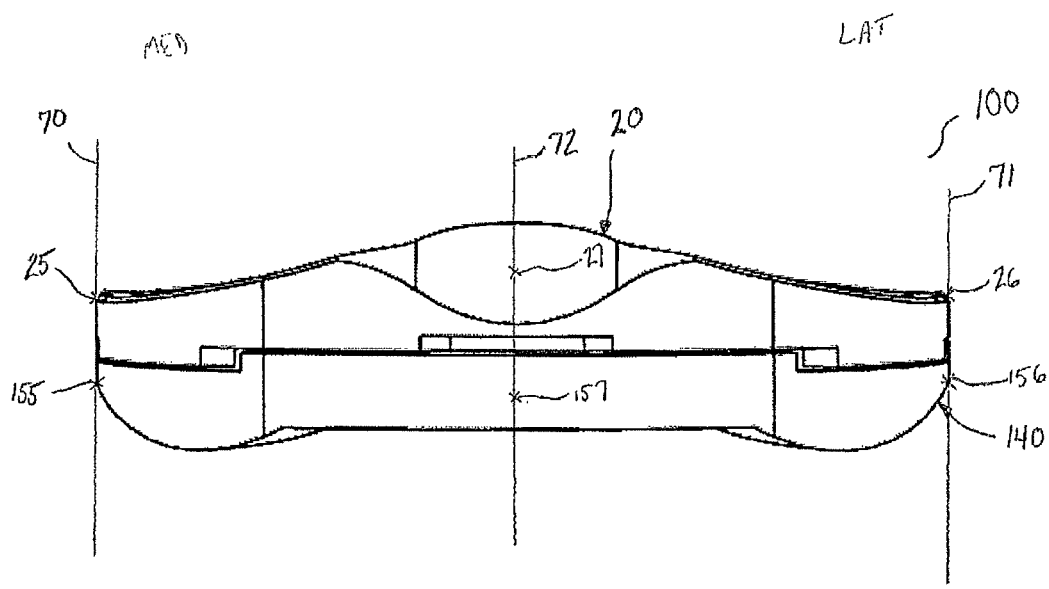
FIG. 7 is a front view of a tibial implant comprised of the tibial baseplate shown in FIG. 4 and the tibial insert shown in FIG. 2.

FIG. 7 illustrates a front view of an embodiment of a tibial implant assembly 100 comprising insert 20 and baseplate 140. Here, a medial axis 70 extends through insert medial apex 25 and baseplate medial apex 155. Similarly, a lateral axis 71 extends through insert lateral apex 26 and baseplate lateral apex 156. Further, a central axis 72 is extends through insert center reference point 27 and baseplate center reference point 157. As shown in the top view of tibial implant assembly 100, shown in FIG. 8, baseplate medial curve 149 and insert lateral curve 29 bend about medial axis 70. Further, baseplate lateral curve 150 and insert medial curve 28 bend about lateral axis 71. Additionally, insert curves 28 and 29 bend about center axis 72 while baseplate curves 149 and 150 bend away from center axis 72.

The respective curves of the tibial implant assembly 100 may have a geometric relationship. For example, in one embodiment insert medial radius 30, insert lateral radius 32, baseplate medial radius 151 and baseplate lateral radius 153 may be essentially equivalent. In an alternate embodiment, insert radii 30 and 32 may be essentially equivalent, baseplate radii 151 and 153 may be essentially equivalent, but the insert radii may be different than the baseplate radii. In yet an alternate embodiment, medial insert radius 30 and baseplate radius 151 may be essentially equivalent, the lateral insert radius 32 and baseplate radius 153 may be essentially equivalent, but respective medial radii may be different than lateral radii. In yet another embodiment, all radii may be different.

Figure 8:
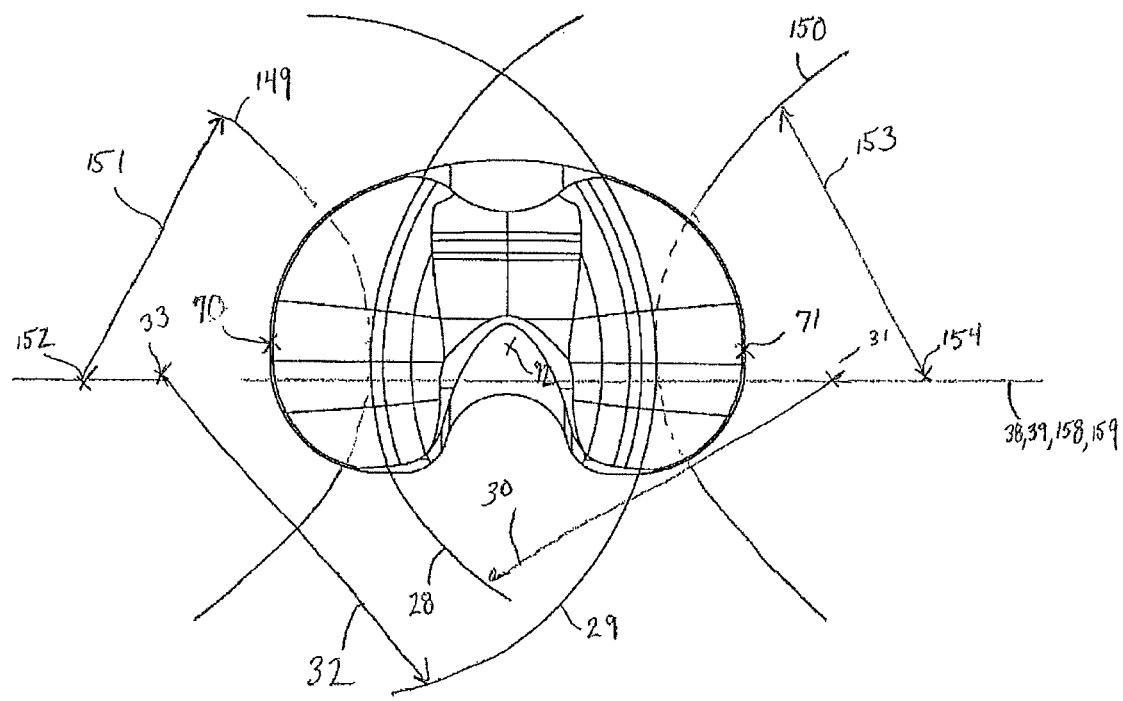
FIG. 8 is a top view of the tibial implant shown in FIG. 7.

Further, regarding the relationship of the curves, the top view of the tibial implant assembly 100 shown in FIG. 8 illustrates a preferred relationship of the curves. Here, insert medial curve 28 and lateral medial curve 149 are essentially tangent from the top view. Similarly, insert lateral curve 29 and baseplate lateral curve 150 are also essentially tangent in this view. In an alternate embodiment, curves may overlap as seen from a top view. For example, baseplate curves 149 and 150 may be more centralized than insert curves 28 and 29. In another embodiment, baseplate curves 149 and 150 may not intersect insert curves 28 and 29 as seen from the top view. Further embodiments may include any combination of overlapping or non-overlapping variations between insert, baseplate, medial and lateral curves.

Similarly, the insert and baseplate planes may have a relationship. In a preferred embodiment, insert planes 38 and 39, and baseplate planes 158 and 159 are aligned and thus shown as a single plane in FIG. 8. In alternate embodiments, the respective planes 38, 39, 158 and 159 may be offset in any combination. For example, baseplate planes 158 and 159 may be offset anteriorly compared to insert planes 38 and 39. In another embodiment, all planes may be offset. In all offset plane combinations, planes 38, 39, 158 and 159 are essentially parallel with respect to each other, yet substantially perpendicular to the center planes CP1 and CP2.

In an alternate embodiment that is not shown, the bone contacting geometry of the baseplate may not be related to the articular geometry of an insert. Here, the baseplate may have any of the structures, or combination of structures previously described. However, the insert concavities may follow a substantially straight path. This may also be described as the respective medial and lateral radii, 30 and 32, having an essentially infinite value. Further, there may be instances where the insert may be relatively flat, therefore not having geometrical concavities. In these embodiments, the bone contacting geometry of the baseplate would still function to increase surface contact area and increase resistance to torsional loading communicated thru the femoral and insert components.

Figure 9:
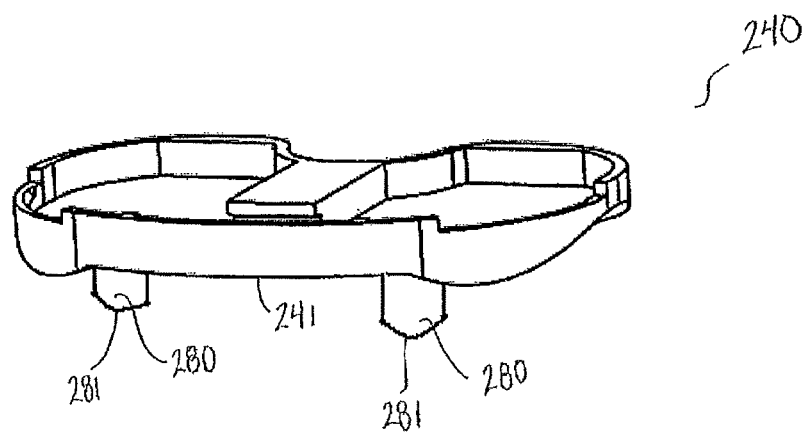
FIG. 9 is a perspective view of a tibial baseplate in accordance with another embodiment of the present invention.

FIGS. 9-13 illustrate alternate embodiments of the present invention. It is understood that each embodiment is comprised of any combination of the insert and baseplate structures previously described. Referring to FIG. 9, a baseplate 240 is shown. In addition to the features previously described, baseplate 240 further comprises pegs 280. Pegs 280 extend distally from the bone contacting surface 241 and have a distal end 281. Pegs 280 are intended to provide additional initial fixation, bone contacting area, resistance to anterior lift-off and rotational constraint to the baseplate implant. The embodiment shown has two pegs 280, however, alternate embodiments may have more than two pegs. Further, although distal end 281 is shown rounded, it may be flat, tapered, conical, or other geometries in alternate embodiments.

Figure 10:
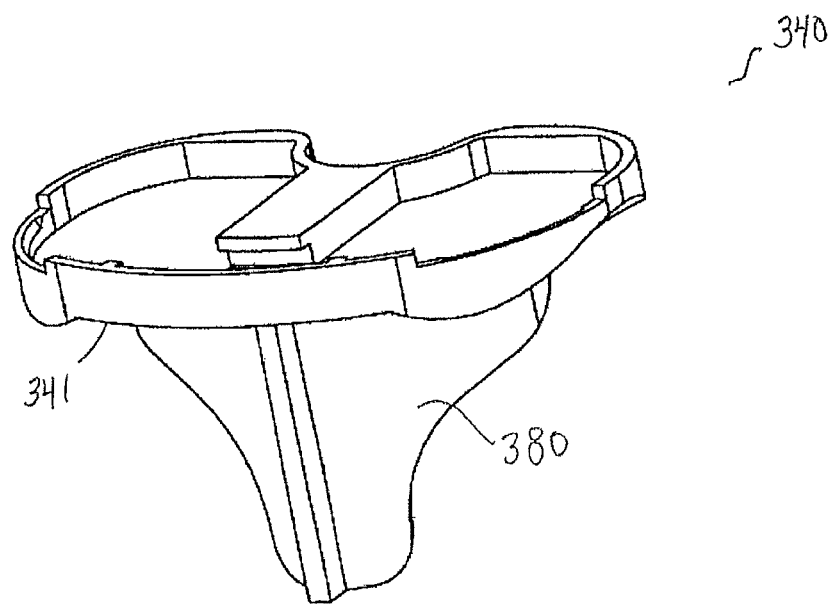
FIG. 10 is a perspective view of a tibial baseplate in accordance with yet another embodiment of the present invention.
Figure 11:
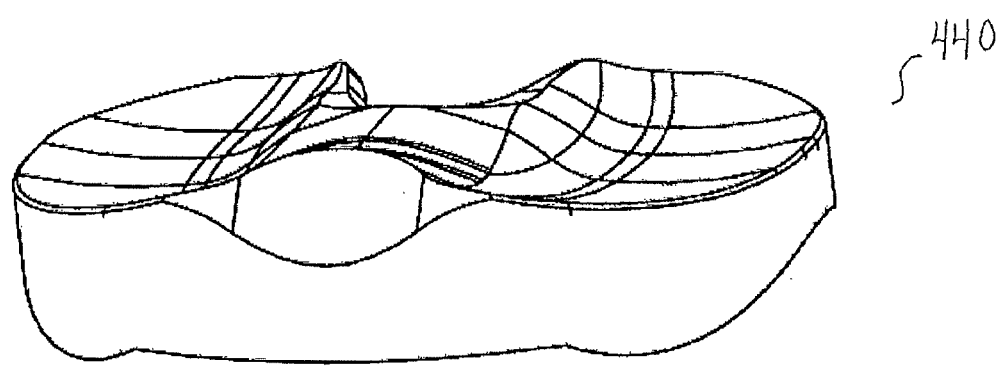
FIG. 11 is a perspective view of a monolithic tibial implant in accordance with another embodiment of the present invention.
Figure 12:
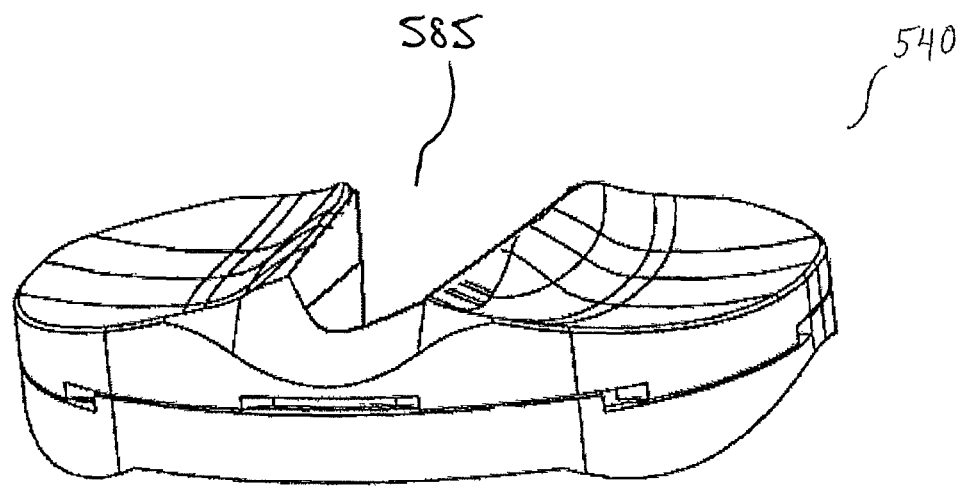
FIG. 12 is a perspective view of a modular bi-cruciate retaining tibial implant in accordance with another embodiment of the present invention, comprised of a tibial baseplate and insert.
Figure 13:
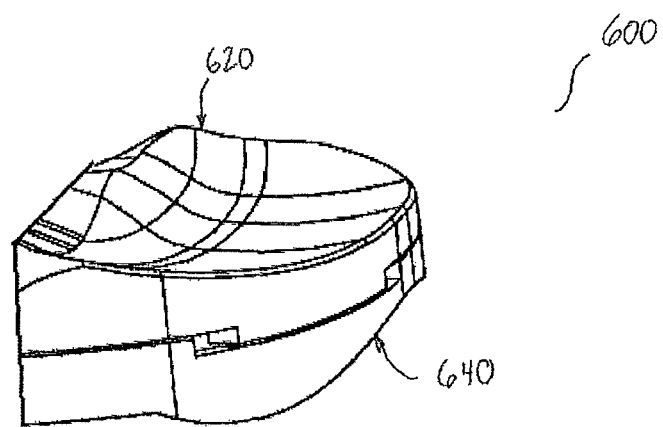
FIG. 13 is a perspective view of a modular unicondylar implant, comprised of a unicondylar baseplate and insert, in accordance with another embodiment of the present invention.

FIG. 10 illustrates a baseplate 340 with a keel 380 extending distally from the bone contacting surface 341. FIG. 11 illustrates a monolithic implant 440 where the baseplate and insert are a single structure manufactured from a material such as polyethelene, PEEK, delrin or other biocompatible materials. FIG. 12 illustrates a baseplate 540 designed for a bi-cruciate retaining arthroplasty procedure. In a bi-cruciate retaining surgery, the patient's ACL and PCL are retained and are encapsulated by an enlarged center channel 585 formed in the baseplate 540. FIG. 13 illustrates a unicompartmental tibial implant assembly 600 comprised of a unicondylar baseplate 640 and unicondylar insert 620.

In all embodiments previously described, the insert components in all embodiments may be manufactured from materials such as polyethylene, PEEK or other known biocompatible materials. All baseplate implants described may be manufactured from materials such as cobalt chrome, titanium, PEEK, polyethylene or other known biocompatible materials. Further, the bone contacting regions of the baseplate implants may be partially or completely covered by beads, porous metal material porous metal or other scaffold-like structure. An example of this material is described in U.S. Patent Application 2006/0147332 titled "Laser Produced Porous Structure", which is hereby incorporated by reference. Further, the bone contacting regions may be treated with hydroxyapetite, periapetite or other osteoinductive material. In cementless procedures, the baseplate implant would preferably include the porous metal material and would directly contact the patient's bone. Alternately, the baseplates may be fixed to the bone using bone cement or other known adhesives for cemented procedures.

New instrumentation and methods may be required to prepare the bone to receive the planar and non-planar implant geometries described above. One method of bone preparation is to use computer controlled or navigated equipment (not shown). Here, rotational bone cutting instruments, such as milling or burring tools, may be used to remove bone in both planar and non-planar regions as required. The computer assisted control allows for accurate preparation and is particularly effective in non-planar resections. Given that the implant geometry is known, a bone preparation software program is developed to instruct the computer on the geometry of the required preparation for each implant size.

Manual instrumentation may also be used to prepare the bone. The manual preparation begins with the known procedural steps of alignment of a planar resection guide. Regarding preparation of the proximal tibial bone, known instruments may be assembled to allow for alignment of a planar resection guide utilizing the tibial plateau, long axis of the tibia and second metatarsal as anatomical reference points. A planar resection is then performed using a standard surgical sawblade. This standard sawblade is substantially flat with a first end that connects to a hand-held power supply and a second end that has a sharp-tooth geometry used for cutting bone. Further of note, the sharp geometry is located within the same theoretical plane as both the first end connection geometry and the sawblade oscillation movement.

Figure 14:
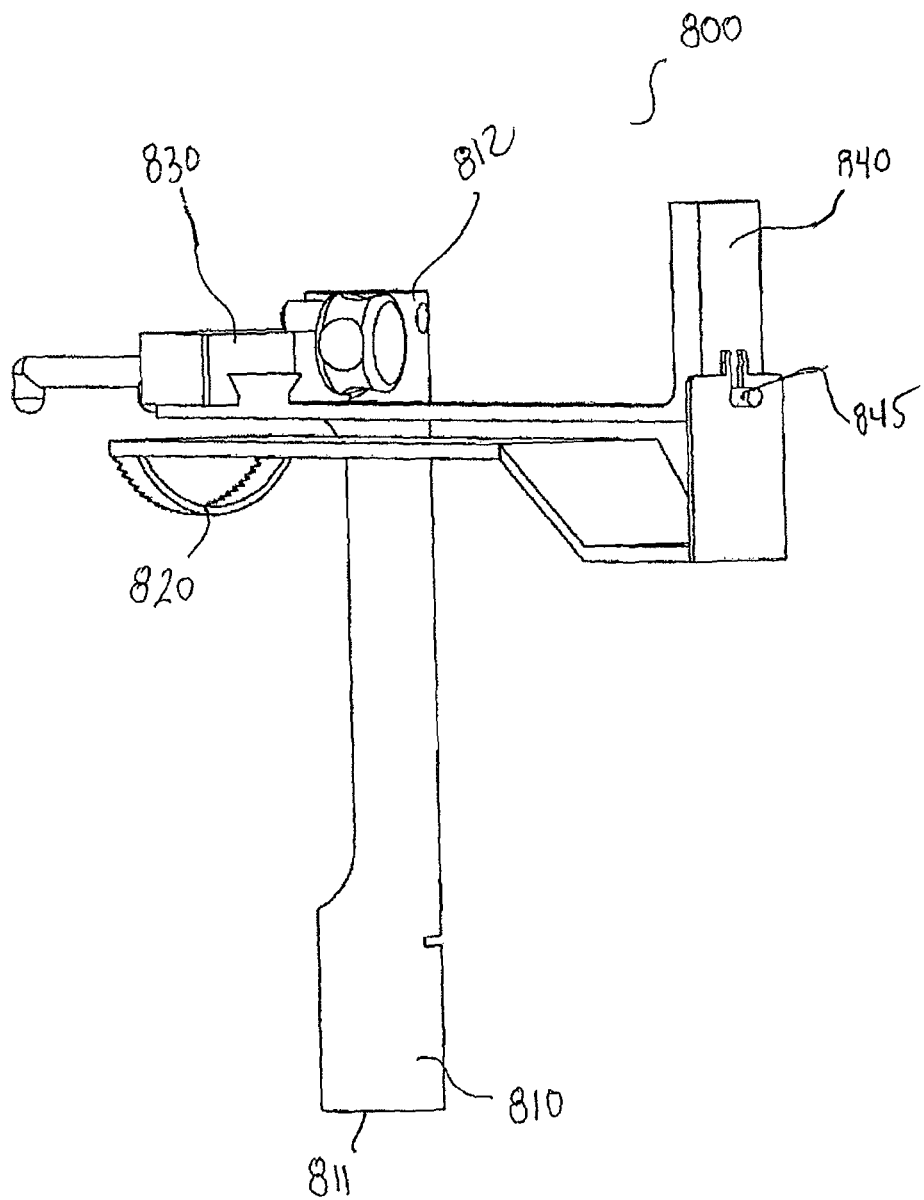
FIG. 14 is a perspective view of an instrument assembly in accordance with one embodiment of the present invention.

FIGS. 14-18 illustrate new manual instrumentation used to prepare the bone to receive the unique curved geometry of the implant as previously described. FIG. 14 is an instrument assembly 800 including a tower 810, a curved sawblade 820, a first guide member 830 and a second guide member 840. The tower includes a distal end 811 which may be connected to extension instruments such as an extension rod or an ankle clamp, and a proximal region 812 preferably used for removable connection to other instruments, such as resection guides.

Figure 15:
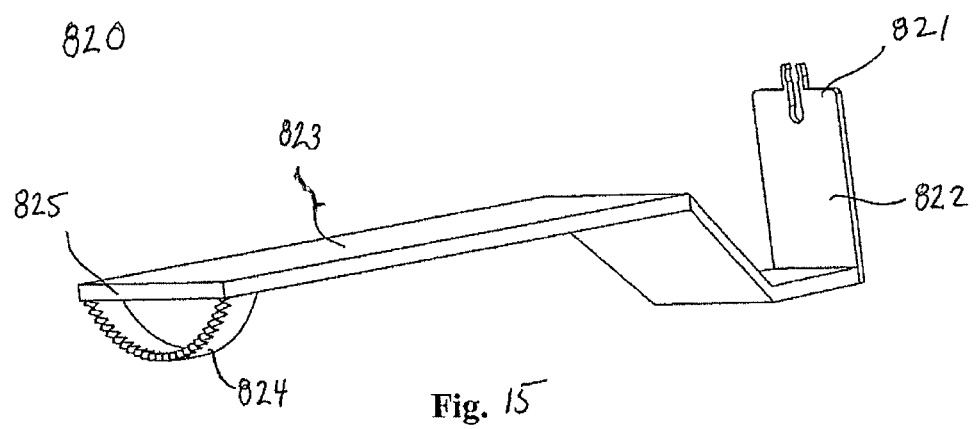
FIG. 15 is a perspective view of a curved sawblade in accordance with one embodiment of the invention.

FIG. 15 illustrates curved sawblade 820 apart from tower 810. Sawblade 820 has a first end 821 which has structures for both connecting to a handle-held power supply and to first guide member 830, a first flat region 822 and a second flat region 823. Of note is that first region 822 and second region 823 are situated within different planes, specifically first region 822 and second region 823 are substantially perpendicular to one another. There are cutting teeth 824 located at a second end 825 of sawblade 820. Cutting teeth 824 are oriented along a curved path, where the curved path corresponds to the convexities 147 and 148 as previously described. Moreover, teeth 824 are not located in the same plane as either flat regions 822 or 823. In alternate embodiments, the path on which the cutting teeth are orientated may be related to other geometries extending from the flat undersurface portion of a baseplate implant.

Figure 16:
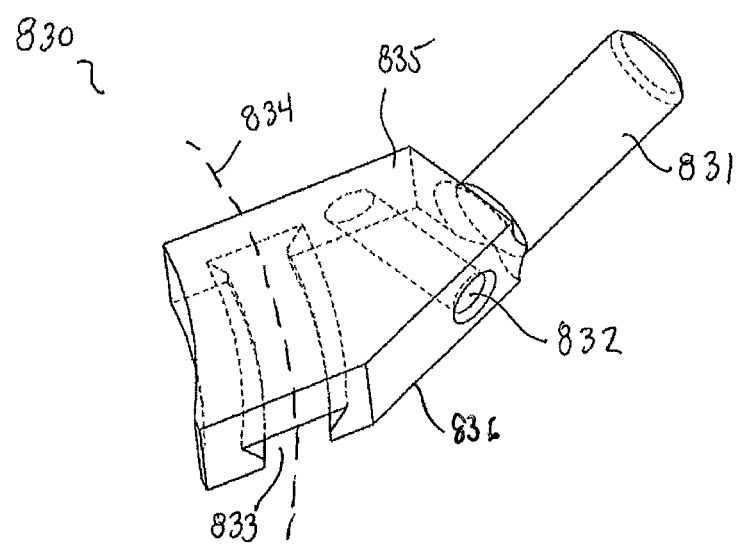
FIG. 16 is a perspective view of a first cutting guide in accordance with one embodiment of the present invention.
Figure 17:
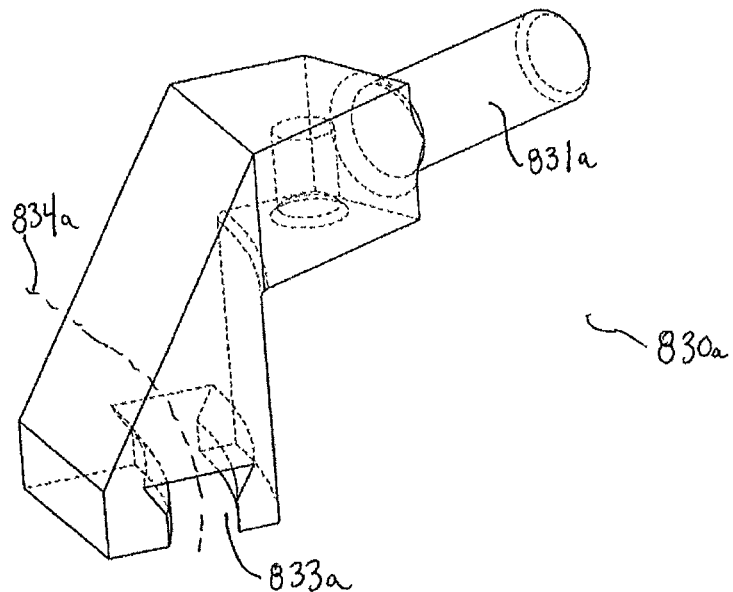
FIG. 17 is a perspective view of an alternate embodiment of the cutting guide illustrated in FIG. 16.

FIG. 16 illustrates one embodiment of first cutting guide 830 apart from the remainder of assembly 800. Guide 830 includes a connection element 831, an aperture 832, a channel 833, a proximal surface 835 and a distal surface 836. Connection element 831 is designed to connect with proximal region 812 of tower 810. Aperture 832 is designed to accept a standard surgical pin for fixation and stabilization with the bone. Channel 833 curves about an axis 834, where axis 834 has a relationship to curves 28 and 29 of the baseplate implant as previously described. It should be noted that channel 833 extends through distal surface 836, but not through proximal surface 835. Further, channel 833 is substantially aligned within a similar theoretical plane as connection element 831. FIG. 17 illustrates an alternate embodiment of a first cutting guide 830a. Guide 830a, has a channel 833a located within a theoretical plane which is substantially offset from a theoretical plane containing connection element 831a. Channels 833 and 833a may have mating geometries, such as angles or undercuts, to facilitate guided connection with second guide 840.

Figure 18:
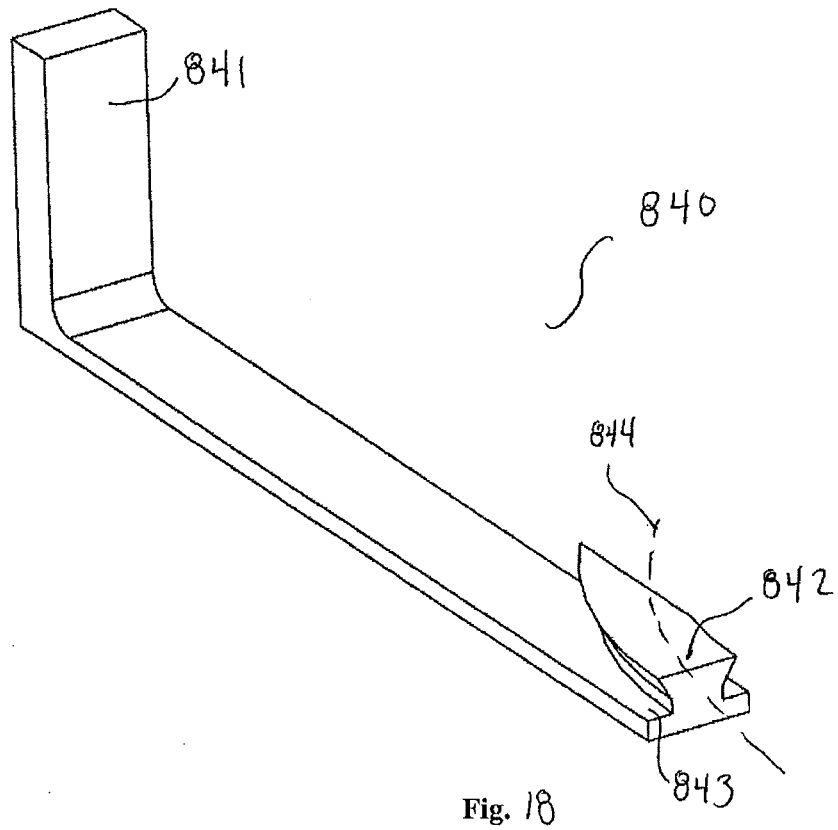
FIG. 18 is a perspective view of a second cutting guide in accordance with one embodiment of the present invention.

FIG. 18 illustrates second guide 840 apart from the remainder of assembly 800. Guide 840 includes a first end 841 and a curved protrusion 842 located on a second end 843. Protrusion 842 curves about an axis 844, where the curvature of axis 844 is identical to axis 834. Protrusion 842 is designed as a mating geometry to allow for movable tracking when engaged with channel 833 of guide 830. A second protrusion 845 (shown in FIG. 14) is designed to mate with first end 821 of sawblade 820.

Figure 19:
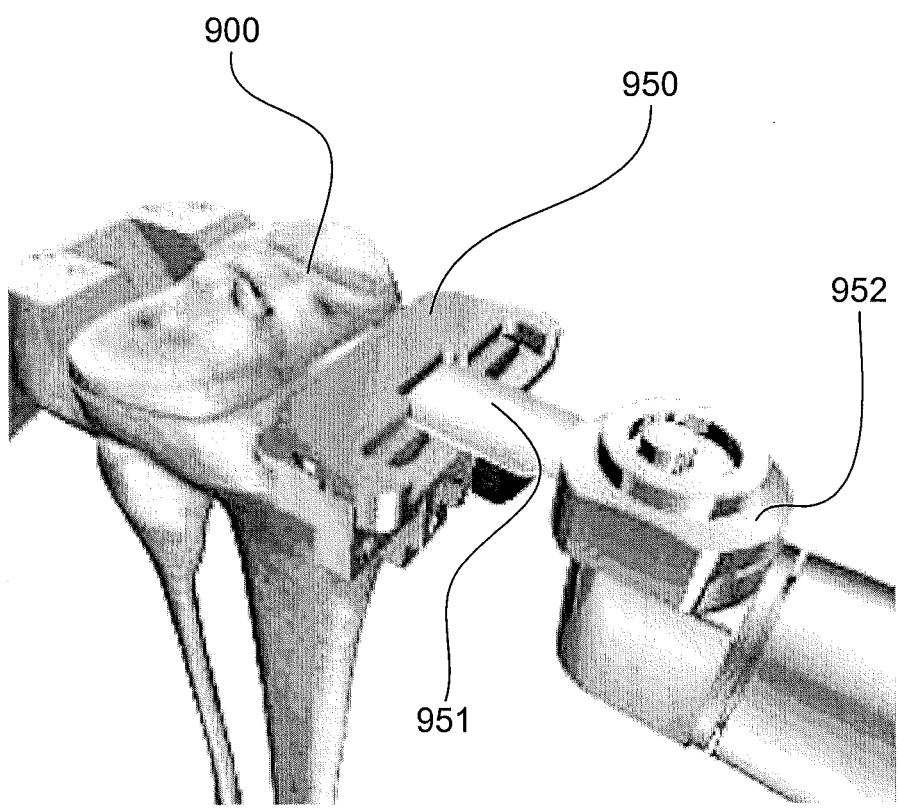
FIG. 19 is a view of a tibial bone and instrumentation associated with the surgical method of planar bone resection.
Figure 20:
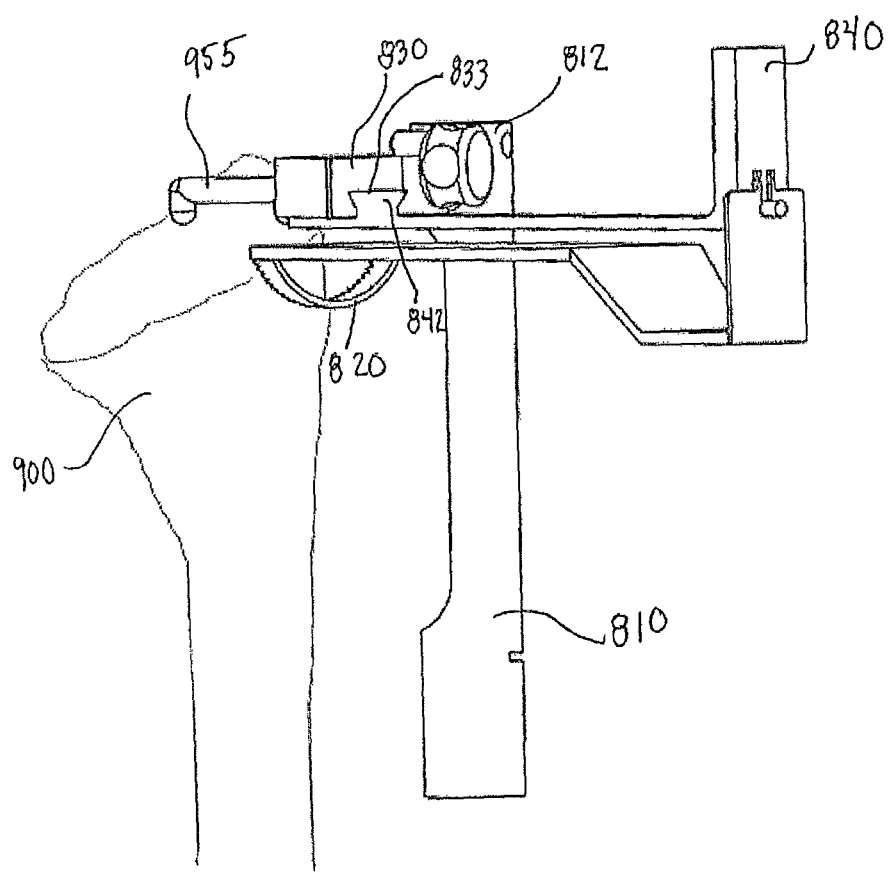
FIG. 20 is a view of a tibial bone, including a planar surface, and instrumentation associated with the surgical method of curved bone resection.
Figure 21:
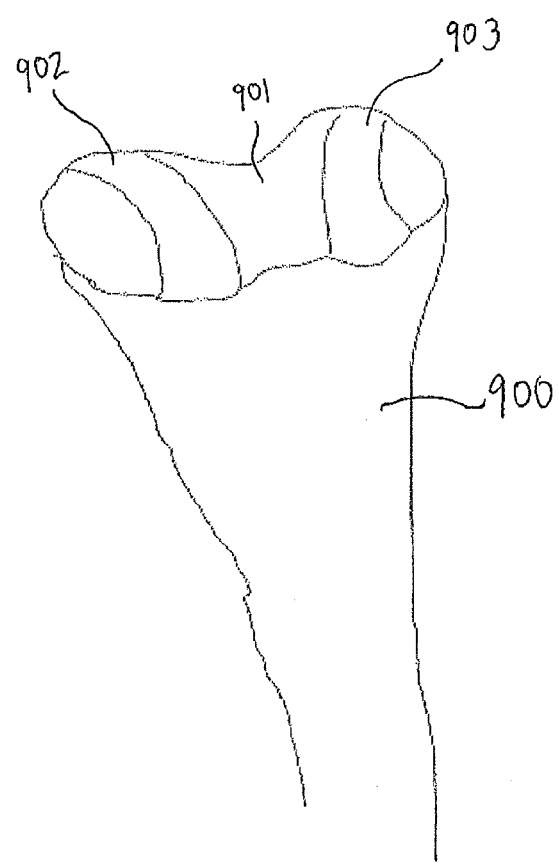
FIG. 21 is a tibial bone including both planar and curved bone resections.

The method of preparing the tibial bone is described in FIG. 19-21. FIG. 19 illustrates a tibial bone 900, planar tibial resection guide 950, standard oscillating sawblade 951 and a hand-held power supply 952. A planar resection of the tibial bone is made by moving sawblade 951 with respect to guide 950 until the resection is complete. Resection guide 950 is then removed from the bone.

Instrumentation required for the curved bone resections is now described. Tower 810 is aligned with the tibial bone. Cutting guide 830 is then connected to proximal region 812 of tower 810. The proximal-distal location relative to the planar bone cut may be determined by use of a known stylus instrument 955 or other means. Guide 830 is fixed relative to the bone by placing a standard pin through aperture 832 (not shown). Next, first end 821 of curved sawblade 820 is connected to a hand-held power supply (not shown). Curved sawblade 820 is then connected to second guide member 840. Protrusion 842 of second guide 840 is movably engaged with channel 833 of first guide 830. FIG. 20 shows assembly 800 oriented with respect to tibial bone 900. The surgeon prepares a first curved resection into the medial side of the tibial bone. Here, the tibial bone resection that extends below the planar resection level and has a concave and curved geometry. The instrumentation assembly may then be reoriented in a similar manner to prepare a lateral curved resection. It should be noted that the lateral curved resection may be completed prior to preparing the medical curved resection. FIG. 21 illustrates tibial bone 900 including regions of planar bone resection 901 and curved bone resections 902 and 903. A tibial implant may then be implanted onto the prepared bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant comprising:
    a bone interface surface having a periphery, a planar region and a first curved surface adjacent the planar region and extending along the implant from the periphery of the bone interface surface at a first location and terminating at the periphery of the bone interface surface at a second location; and
    an articular surface disposed opposite the bone interface surface and having a second curved surface located at least partially within a periphery of the articular surface,
    wherein the first curved surface is convex so as to extend in a direction away from and a direction perpendicular to the planar region and away from the articular surface,
    wherein the first curved surface intersects the planar region at an interface, said interface, due to the curvature of the first curved surface, extends along an arcuate path from the first location to the second location, and
    wherein the first curved surface has a first center of curvature and a first radius extending between the first curved surface and first center of curvature, the bone interface surface has a first apex and the articular surface has a second apex, and the first and second apexes define an axis extending therethrough and the first curved surface curves about the axis.

2. The implant of claim 1, wherein the second curved surface curves away from the axis and has a second center of curvature and a second radius extending between the second curved surface and second center of curvature.

3. The implant of claim 2, wherein the first and second curved surfaces are curved along the implant such that the first and second curved surfaces are each tangent to a sagittally oriented plane extending through the articular and bone interface surfaces.

4. The implant of claim 2, wherein the first curved surface is curved along the implant such that the first center of curvature is located within a first coronally oriented plane, and the second curved surface is curved along the implant such that the second center of curvature is located within a second coronally oriented plane, the first and second coronally oriented planes being essentially aligned.

5. The implant of claim 2, wherein the first curved surface is curved along the implant such that the first center of curvature is located within a first coronally oriented plane, and the second curved surface is curved along the implant such that the second center of curvature is located within a second coronally oriented plane, the first and second coronally oriented planes being offset.

6. The implant of claim 2, wherein the first and second curved surfaces are curved along the implant such that the first radius has a length equivalent to the length of the second radius.

7. The implant of claim 2, wherein the first and second curved surfaces are curved along the implant such that the length of the first radius is different from the length of the second radius.

8. The implant of claim 1, wherein the first curved surface is curved along the implant such that the axis is located between the first curved surface and first center of curvature.

9. The implant of claim 1, wherein the periphery is defined by a perimeter of the bone interface surface, and the implant is designed to replace a portion of the proximal tibia.

10. The implant of claim 1, wherein the bone interface surface further includes a third curved surface adjacent the planar region and extending along the implant from the periphery of the bone interface surface at one location and terminating at the periphery of the bone interface surface at another location, the third curved surface being convex so as to extend in a direction away from and perpendicular to the planar region, the first and third curved surfaces being separated by the planar region.

* * * * *